United States Patent [19]
Elsheikh

[11] Patent Number: 5,208,395
[45] Date of Patent: May 4, 1993

[54] MANUFACTURE OF HYDROFLUOROCARBONS

[75] Inventor: Maher Y. Elsheikh, Tredyffrin, Pa.

[73] Assignee: Elf Atochem North America, Inc., Philadelphia, Pa.

[21] Appl. No.: 866,772

[22] Filed: Apr. 6, 1992

[51] Int. Cl.$^5$ .............................................. C07C 17/08
[52] U.S. Cl. ................................................... 570/166
[58] Field of Search ................................ 570/170, 166

[56] References Cited

U.S. PATENT DOCUMENTS 2,749,374  6/1956  Ruh et al. ............................. 570/170
3,904,701  9/1975  Schultz et al. ....................... 570/166

FOREIGN PATENT DOCUMENTS 608111  9/1948  United Kingdom ................ 570/160

Primary Examiner—Alan Siegel

[57] ABSTRACT

A novel, heterogeneously-catalyzed, gas phase process for the production of 32 and 152a which comprises contacting the corresponding 1,1-dichloroalkane and HF in the vapor phase in the presence of a Lewis acid catalyst such as tin tetrachloride.

3 Claims, No Drawings

MANUFACTURE OF HYDROFLUOROCARBONS

FIELD OF THE INVENTION

The present invention relates to the manufacture of 1,1-difluoromethane ("32") and 1,1-difluoroethane ("152a") by fluorination of the corresponding 1,1-dichloroalkane. More particularly, it relates to a heterogeneous gas phase catalyzed fluorination of dichloromethane ("30") or 1,1-dichloroethane ("150a") with hydrogen fluoride, using Lewis acids, to produce the corresponding 1,1-difluoroalkane.

BACKGROUND OF THE INVENTION

The hydrofluorocarbons ("HFCs") 32 and 152a have zero ozone depletion potential and low global warming potential, making them environmentally acceptable as refrigerants. HFC 152a is also a potential foam blowing agent for the plastics industry.

The dichloromethyl group of 30 and 150a is highly unreactive for hydrofluorination processes and its Lewis acid catalyzed fluorination in prior art liquid phase reactions has been shown to require a strong Lewis acid such as an antimony halide [U.S. Pat. No. 2,749,374; CA83(25):205901e; and CA83(25):205754j]. What is needed is a method for the efficient production of these HFCs which is suitable for large scale commercial exploitation.

SUMMARY OF THE INVENTION

A heterogeneous gas phase catalysis for producing 32 or 152a is provided. A 1,1-dichloroalkane selected from 30 or 150a is contacted with hydrogen fluoride in the vapor phase, in the presence of an unsupported or supported Lewis acid catalyst selected from tin or bismuth salts (preferably tin tetrachloride supported on an activated carbon support), to form the corresponding 1,1-difluoroalkane (32 or 152a).

DETAILED DESCRIPTION OF THE INVENTION

It has now been unexpectedly found that certain relatively weak Lewis acid catalysts, such as tin (IV) salts, are effective in the gas phase to fluorinate the dichloromethyl group of 30 and 150a.

The process of this invention may be utilized in either batch or, preferably, continuous fashion. Generally, the hydrogen fluoride and dichloroalkane are contacted in the vapor phase at a molar ratio of from about 0.5:1 to about 10:1, preferably from about 2:1 to 5:1.

The process may be operated at any temperature which favors the conversion of both the chloro groups to fluoro groups. Generally, the process is operated between from about room temperature, 22 degrees Centigrade ("C"), to about 600 degrees C., preferably from about 22° to 200° C. for converting 150a to 152a and about 200° to 400° C. for converting 30 to 32. The optimum residence time is a dependent variable, but is typically from about 10 to about 300 seconds (preferably from about 60 to about 100 seconds for 32 and from about 100 to about 200 seconds for 152a).

The reaction is generally carried out at atmospheric pressure, in the presence of a catalyst selected from tin (IV) and bismuth (III) salts, preferably chlorides. The chlorides are converted to the corresponding fluorides upon activation with hydrogen fluoride. The catalyst may be used directly or may be carried on an appropriate support, such as activated carbon. Such supported catalysts may be employed, for example, in the form of pellets or granules.

Tin tetrachloride on activated carbon is a particularly useful catalyst. Upon HF activation, the resulting solid tin tetrafluoride remains strongly adhered to the carbon support, without leaching of the catalyst bed.

The process may be utilized with or without an inert carrier gas. If a carrier gas is used, the preferred gas is nitrogen, in the amount of from about 10 to about 100 volume percent based upon the total volume of the reactants. Other suitable inert carrier gases are known to the art.

The process may be carried out in a batch or continuous fashion. In the preferred continuous mode, the gaseous hydrogen fluoride and gaseous dichloroalkane are typically continuously fed into a reactor (usually tubular in design) in the presence of the catalyst, and the reaction product (that is, the corresponding difluoroalkane) is continuously withdrawn from the reactor and passed to a suitable scrubbing tower for removal of HF by the action of a countercurrent alkaline stream (which may comprise, for example, 1.5 normal potassium hydroxide; other aqueous hydroxides such as sodium hydroxide or calcium hydroxide may also be utilized). The scrubbed product is then passed to a drying tower, packed with a suitable drying agent such as anhydrous calcium sulfate.

The materials of construction of the reactor are not critical, except that they should possess the necessary structural and physical characteristics to withstand the reaction conditions.

The present invention is illustrated in more detail below by reference to the following non-limiting examples. Preferred conditions are not necessarily used in the examples, which are intended to show the effect of varying the process conditions such as contact time, temperature, and the like. All temperatures are in degrees Centigrade.

EXAMPLE 1

Fluorination of 30 to 32

A catalyst comprised of tin tetrachloride absorbed on a bed of activated carbon (117 grams containing 0.0017 mole of tin tetrachloride per gram of catalyst) was loaded into a tubular reactor and activated for 18 hours at 50 degrees using 5 cc/min. of nitrogen, followed by HF activation at 50 degrees using 20 ml/min. of HF for 18 hours. The process was evaluated at various temperatures using an HF to 30 ratio of about 5.2:1. The product was scrubbed, dried, and analyzed with a gas chromatograph ("G.C."). The G.C. results (reported in area %) were as follows:

| Temp. | Contact Time | Conversion (%) | % 32 |
| --- | --- | --- | --- |
| 150 | 51 sec. | 18.8 | 12.0 |
| 200 | 43 sec. | 21.3 | 27.8 |
| 200 | 87 sec. | 22.9 | 23.1 |
| 250 | 87 sec. | 41.7 | 59.3 |

EXAMPLE 2

Fluorination of 150a to 152a

Using 85.5 grams of the same catalyst, and activating it as in Example 1, the process was evaluated at various temperatures, mole ratios, and contact times. Following scrubbing and drying, the product was analyzed with the following G.C. results (in area %):

| Temp. | HF:150a | Contact Time | Conv. (%) | % 152a |
|-------|---------|--------------|-----------|--------|
| 51 | 0.7:1 | 153 sec. | 43.2 | 18.7 |
| 51 | 1.1:1 | 121 sec. | 49.8 | 17.5 |
| 75 | 1.1:1 | 107 sec. | 61.7 | 32.4 |
| 75 | 2.0:1 | 75 sec. | 78.3 | 74.5 |

What is claimed is:

1. A heterogeneously catalyzed gas phase process for producing 1,1-difluoromethane or 1,1-difluoroethane comprising contacting hydrogen fluoride and the corresponding 1,1-dichloroalkane in the vapor phase in the presence of a solid catalyst consisting of tin tetrafluoride supported on activated carbon.

2. A process as in claim 1 wherein the 1,1-dichloroalkane is dichloromethane.

3. A process as in claim 1 wherein the 1,1-dichloroalkane is 1,1-dichloroethane.

* * * * *